(12) United States Patent
Belmonte et al.

(10) Patent No.: US 9,132,205 B2
(45) Date of Patent: Sep. 15, 2015

(54) DISPENSING DEVICE FOR AIR TREATMENT AGENTS

(75) Inventors: Elias Belmonte, Montvale, NJ (US); Wu Jin, Hull (GB); Matthew Copeman, Hull (GB); Steve Walsh, Hull (GB)

(73) Assignee: Reckitt Benckiser (UK) Limited, Slough, Berkshire (GB)

(*) Notice: Subject to any disclaimer, the term of this patent is extended or adjusted under 35 U.S.C. 154(b) by 436 days.

(21) Appl. No.: 12/513,733

(22) PCT Filed: Dec. 5, 2007

(86) PCT No.: PCT/GB2007/004663
§ 371 (c)(1),
(2), (4) Date: May 6, 2009

(87) PCT Pub. No.: WO2008/068486
PCT Pub. Date: Jun. 12, 2008

(65) Prior Publication Data
US 2010/0143186 A1 Jun. 10, 2010

(30) Foreign Application Priority Data
Dec. 6, 2006 (GB) .................................. 0624371.1

(51) Int. Cl.
*A61L 9/03* (2006.01)
*A61L 9/12* (2006.01)
(52) U.S. Cl.
CPC ................ *A61L 9/037* (2013.01); *A61L 9/122* (2013.01); *A61L 9/127* (2013.01)
(58) Field of Classification Search
CPC ..................................... A61L 9/03; A61L 9/12
USPC ............................................. 422/3, 105, 109
See application file for complete search history.

(56) References Cited

U.S. PATENT DOCUMENTS

2007/0012181 A1* 1/2007 Niezgoda et al. .................. 95/1

FOREIGN PATENT DOCUMENTS

| DE | 10327859 A | 1/2005 |
| FR | 2689399 A | 10/1993 |

(Continued)

OTHER PUBLICATIONS

English Language Abstract for JP2004141618 taken from esp@cenet.com, May 2004.

(Continued)

*Primary Examiner* — Sean E Conley
(74) *Attorney, Agent, or Firm* — Norris McLaughlin & Marcus PA

(57) ABSTRACT

The present invention relates to a dispensing device for at least one air treatment agent comprising at least one airborne agent detector operable to detect airborne agents in the air; receiving means for receiving at least one source of air treatment agent; and control means for releasing an amount of at least one air treatment agent from a source thereof received in the receiving means when a current airborne agent level detected by the airborne agent detector deviates from a background airborne agent level detected by the airborne agent detector by more than a predetermined amount, wherein the background airborne agent level is calculated by the device. The present invention also relates to a method of dispensing at least one air treatment agent.

27 Claims, 1 Drawing Sheet

(56) References Cited

FOREIGN PATENT DOCUMENTS

| | | |
|---|---|---|
| GB | 2295091 A | 5/1996 |
| GB | 2405097 A | 2/2005 |
| JP | 04017858 A | 2/1992 |
| JP | 2004141618 A | 5/2004 |
| WO | 0225180 A | 3/2002 |
| WO | 2004037304 A | 5/2004 |
| WO | 2004062700 A | 7/2004 |
| WO | 2005018690 A | 3/2005 |

OTHER PUBLICATIONS

English Language Abstract for DE10327859 taken from esp@cenet.com, Jan. 2005.

English Language Abstract for FR2689399 taken from esp@cenet.com, Oct. 1993.

English Language Abstract for JP4017858 taken from esp@cenet.com, Feb. 1992.

* cited by examiner

DISPENSING DEVICE FOR AIR TREATMENT AGENTS

This is an application filed under 35 USC 371 of PCT/GB2007/004663.

This invention relates to a dispensing device for air treatment agents, especially for use in deodorising or neutralising odours in an air space.

Air fresheners and other air treatment agents are widely used in many applications, in houses, vehicles and elsewhere. Automated air fresheners have been proposed, in which a dispensing mechanism turns on and off periodically; set by a user. These systems are adequate when it is possible to predict when dispensing of the active agents is needed; but is inadequate if for example malodour or other substances enter an atmosphere at non-regular intervals.

Efforts have been made to design an air freshener, which dispenses fragrance, deodorant or sanitizing agent only when a room is occupied, and which utilises infrared detectors to detect movement within a room or air space.

The need for efficient non-regular or regular release of air freshener is equally applicable to other active ingredients such as odour neutralisers and anti-bacterial agents.

It is an object of the invention to address the above mentioned disadvantages.

According to a first aspect of the present invention, there is provided a dispensing device for at least one air treatment agent, the dispensing device comprising at least one airborne agent detector operable to detect airborne agents in the air; receiving means for receiving at least one source of air treatment agent; and control means for releasing an amount of at least one air treatment agent from a source thereof received in the receiving means when a current airborne agent level detected by the airborne agent detector deviates from a background airborne agent level detected by the airborne agent detector by more than a predetermined amount, wherein the background airborne agent level is calculated by the device.

Preferably the device comprises a single airborne agent detector arranged to target the concentration of chemical compounds in the environment surrounding the device.

Preferably, the control means are operable to calculate the current airborne agent level by calculating an average of a predetermined number of most recent readings of the detector. Preferably, two to five of the most recent readings, more preferably three of the most recent readings.

The control means may be operable to calculate the deviation of the current airborne agent level from the background level by means of a subtraction of one from the other, and/or by means of a ratio of one to the other.

Preferably, the deviation is calculated by subtracting the background level from the current airborne agent level and dividing that amount by the background level value. The result may be multiplied by a constant, for ease of display and/or use.

Unlike several known prior art device the device of the present invention does not operate using a pre-defined value for the background airborne agent level, rather the device of the present invention calculates this level and uses this calculated level to control the release of the at least one air treatment agent. This arrangement may be advantageous as the device is operable to adapt how it releases the one or more air treatment agent depending on the characteristics of the surrounding environment in which it is used.

Preferably, the control means are operable to calculate the background airborne agent level by calculating an average of a longer time period than that over which the current airborne agent level is calculated.

Preferably, the background airborne agent level and the current airborne agent level are temporally offset, preferably by at least 5 seconds, more preferably by at least 10 second, more preferably by at least 20 seconds.

Once the device is placed into an operational mode, the background airborne agent level may be an average of the levels of airborne agent detected by the device throughout the duration of that operational mode. In this arrangement the device may better 'learn' the characteristics of its local environment and, during use, will be better able to provide for the release of an air treatment agent(s) when the current airborne agent level deviates from the background level by more than the predetermined amount. If a user wishes to move the device to an alternative location, a user may be encouraged to disengage the device from the operational mode, this disengagement may have the effect of resetting the average levels of background agent such that the device is operable to 'learn' the characteristics of its new environment when placed back into the operational mode by calculating the average background agent level from no existing starting point.

Preferably, the control means are operable to calculate the background airborne agent level by calculating an average of a predetermined number of some or all of the most recent readings of the detector. Preferably 10 to 10,000 of the most recent readings, more preferably 20 to 5,000 of the most recent readings, and most preferably 50 to 1000 of the most recent readings.

The device may be provided with an initial setting mode wherein when the device is first powered up, the control means will automatically calibrate based on the existing background odour when the device is first switched on.

In an alternative or additional arrangement, the control means are preferably operable to calculate the background level based on calculating a series of averages from rolling windows of measurements from the detector. Each rolling window may be an average of between two and ten readings, preferably six readings. Preferably, the windows do not overlap. Preferably, the windows span a time period of between 5 and 30 minutes, preferably between 10 and 25 minutes, preferably between 15 and 20 minutes. There may be approximately 30 to 50 windows.

Preferably, the control means are operable to discard the oldest window when a new window becomes available, preferably taking into account an offset between the current and background levels.

Preferably, the control means are operable to adjust the predetermined level of deviation from the background level that results in air treatment agent being released. The predetermined level may be manually adjustable. The deviation may be a positive or negative deviation.

The control means may be operable to activate emanation acceleration means, which may be a heater and/or a fan, of the device adapted to accelerated emanation of at least one air treatment agent. Preferably, a heater is adapted to heat a wick to accelerate evaporation of at least one air treatment agent. The heater may have two or more heating elements.

Preferably, a first heating element is adapted to provide a first level of dispensing of at least one air treatment agent. Preferably, a second heating element and/or the first heating element given more current and/or a fan, is adapted to provide a boost to the emanation of the at least one air treatment agent, based on the current and background levels discussed above.

Alternatively, the control means may be adapted to disperse a first air treatment agent, preferably substantially continuously or during a periodic cycle, and for a second air treatment agent to be dispersed on detection of a deviation of the current level from the background level. The first air treatment agent may be a fragrancing agent. The second air treatment agent may be a deodorising agent, or a fragrancing agent, or an insect repelling agent.

The control means preferably incorporates a sensor heater control unit adapted to provide power, preferably a steady flow of power, to the airborne agent detector. The airborne agent detector may be a variable resistor, for which resistance varies according to ambient airborne agents.

The control means preferably incorporates a load resistance network adapted to select a load for supply to the airborne agent detector.

The control means preferably incorporates a boost heat control unit adapted to determine whether the second heating element and/or fan should be operated.

The control means is preferably pre-programmed with particular settings. For example, the sensor may be limited to one boost per half hour period, but of course this could be set to a different threshold if required. Such adjustment of the threshold will prevent the air treatment agent being consumed too quickly in use of the device.

The device may be provided with a switch to allow a user to change the boost threshold to prevent the dispenser boosting too often or not enough. The control means may be programmed with a booster target, for example which may be three boosts per day that is based on a deviation of the sensed odour level from a sensed background level. The user may be able to set, for example, a low, medium or high threshold, with a low threshold, for example, being just one boost per day against a measured background, whereas a high setting may be eight to twelve boosts a day for a given background level of odour.

The device may be provided with a user-controlled boost mechanism. In use of the device, the activation of said boost mechanism may substantially immediately cause the dispensing of the at least one air treatment agent.

The dispensing device may comprise a source of at least one air treatment agent. The dispensing device may comprise sources of first and second air treatment agents, which may be contained in a single container or separate containers.

Each source of air treatment agent preferably has its own heater and/or fan to assist dispensing. Each source preferably has its own wick to receive heat and to assist emanation.

The airborne agents may be odours, which may be malodours or may be for example cooking odours, or may be perfumes or other airborne chemicals.

According to a second aspect of the present invention there is provided an automated method for dispensing at least one air treatment agent comprising releasing an amount of at least one air treatment agent from a source thereof received in a dispensing device, wherein control means of the device detect if a current airborne agent level detected by an airborne agent detector deviates from a background airborne agent level detected by the airborne agent detector by more than a predetermined amount, wherein said background level is calculated by the device.

Preferably the method detects the concentration of chemical compounds in the environment surrounding the device to calculate the levels of airborne agents.

Preferably, the current airborne agent level is calculated by calculating an average of a predetermined number of most recent readings of the detector. Preferably, four to eight of the most recent readings, more preferably six of the most recent readings.

Preferably, the background airborne agent level is calculated by calculating an average of a longer time period than the current airborne agent level.

Preferably, the background airborne agent level and the current airborne agent level are temporally offset, preferably by at least 5 seconds, more preferably by at least 10 second, more preferably by a least 20 seconds.

Once the device is placed into an operational mode, the background airborne agent level may be an average of the levels of airborne agent detected during the method by the device throughout the duration of that operational mode.

Preferably, the control means are operable to calculate the background airborne agent level by calculating an average of a predetermined number of some or all of the most recent readings of the detector. Preferably 10 to 10,000 of the most recent readings, more preferably 20 to 5,000 of the most recent readings, and most preferably 50 to 1000 of the most recent readings, and ideally 100 to 500 of the most recent readings.

In an alternative or additional arrangement, the control means are preferably operable to calculate the background level based on a series of averages from rolling windows of measurements from the detector. Each rolling window may be an average of between two and ten readings, preferably six readings. Preferably, the windows do not overlap. Preferably, the windows span a time period of between 5 and 30 minutes, preferably between 10 and 25 minutes, preferably between 15 and 20 minutes. There may be approximately 30 to 50 windows.

Preferably, the oldest window is discarded when a new window becomes available, preferably taking into account an offset between the current and background levels.

Preferably, the predetermined level of deviation from the background level that results in air treatment agent being released is adjustable. The predetermined level may be manually adjustable. The deviation may be a positive or negative deviation.

Any of the features described herein may be combined with any of the above aspects in any combination.

For a better understanding of the invention, and to show how embodiments of the same may be carried into effect, reference will now be made, by way of example, to the accompanying diagrammatic drawings in which.

Devices using chemical-specific, or odour-specific sensors for airborne contaminants have already been disclosed. However, it has been realised that the cost of such devices and their sensitivity and accuracy or indeed their specificity is disadvantageous. Therefore, in order to address that issue, it has been realised that a non-specific sensor (or sensors) that detects changes in the concentration of chemical contaminants in the air, which chemicals are sensed as odours, fragrances and the like is a cost effective sensor(s) to use with a dispenser for air treatment agents.

Figure 1:
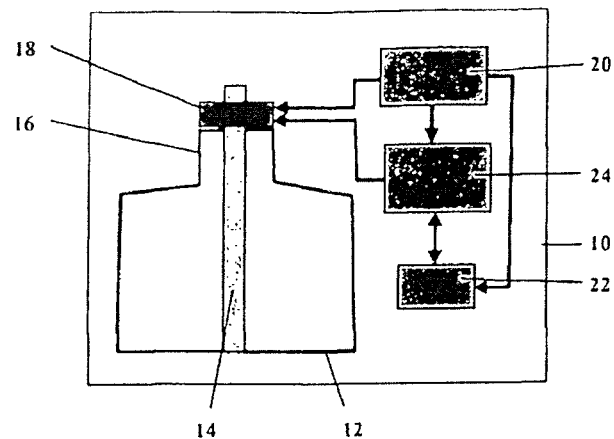
FIG. 1 shows a schematic cross-sectional side view of a dispenser for air treatment agents.

FIG. 1 shows an air treatment agent dispenser 10 having an air treatment agent container 12 into which extends a wick 14. Above a neck 16 of the container there is located a heater block 18, which may be in the form of a ceramic material containing at least one resistor (HR in FIG. 2) that forms part of an electrical heating circuit having a power supply 20.

The dispenser 10 also includes a chemical sensor 22 that responds to changes in the concentration of chemicals in the air, including odours.

The dispenser 10 also incorporates a controller 24 that is operable to receive signals from the sensor 22 and to provide control of the heater block 18 and an optional dispersing fan located close to a section of the wick 14 that protrudes above the heater block 18.

The heater block 18 incorporates an additional resistor HB for additional heat that is used in order to provide a boost of air treatment agent from the container 12 as and when dictated by the controller 24.

In more detail, the sensor discussed hereinafter is a tin oxide chemical sensor, for example such as the TGS 2600 Model supplied by Figaro, for those supplied by UST and FIS. Such sensors are currently used in vehicles, gas sensing equipment, for CO detection and air quality testing. This type of sensor detects airborne chemicals, which will include both perfumes and a malodour for example. Such sensor(s) function by a chemical in the air or malodour being absorbed onto the surface of the sensor, the chemical is oxidised or reduced, depending on the nature of the chemical. This process changes the oxidation level of the sensor surface and this changes the electrical conductivity/resistivity of the sensor, depending on the type of sensor used. By measuring the magnitude of the conductivity/resistivity change the sensor can be used to measure the concentration of chemicals in the air using suitable calibration.

Although not described in detail, other types of odour sensor(s) may be used within the devices and methods of the present invention however.

For the chemical sensor(s) it has been found to be advantageous to measure simply a concentration of chemicals in the air, rather than targeting specific chemical compounds, which would require multiple sensors and also is an extremely difficult undertaking. In particular, the number of different compounds in a single odour can be great, and may require too great a number of sensors to be practical in a device such as an air treatment agent dispenser.

The device is primarily used with an air freshening composition, but could equally be used with an odour removing preparation, or a sanitising preparation. The use of the two stage heater referred to above may be linked to the use of the fan. Alternatively, only the two heating elements may be used without the presence of the fan in the device.

The controller 24 may be set to trigger a boost in fragrancing by use of the second resistor in the heater block 18 when positive or negative sensor signals are detected i.e. a deviation from a set background level (discussed below) of resistivity/conductivity of the sensor is reached. A positive signal will represent an increase in odour level and a negative signal will represent a reduction in odour level, caused for example by a window or door being opened. It can be beneficial to provide a boost when the level of detection is reduced, in order to maintain a consistent fragrance level in the vicinity of the dispenser. This is relevant to a person's habituation to odours, which may require that a minimum level of the fragrance is required to ensure that the person can smell the fragrance.

The controller 24 is pre-programmed with particular settings. For example, the sensor will be limited to one boost per half hour period, but of course this could be set to a different threshold if required. Such a threshold will prevent the fragrance in the container 12 being consumed too quickly.

The dispenser may be provided with a switch to allow a user to change the boost threshold to prevent the dispenser boosting too often or not enough. The controller 24 may be programmed with a booster target, for example which may be three boosts per day that is based on a deviation of the sensed odour level from a sensed background level, as discussed below. The user may be able to set for example a low, medium or high threshold, with a low threshold, for example, being just one boost per day against a measured background, whereas a high setting may be eight to twelve boosts a day for a given background level of odour.

The controller 24 is also programmed such that there is an initial setting mode when the device is first powered up which will automatically calibrate based on the existing background odour where the device is first switched on.

Figure 2:
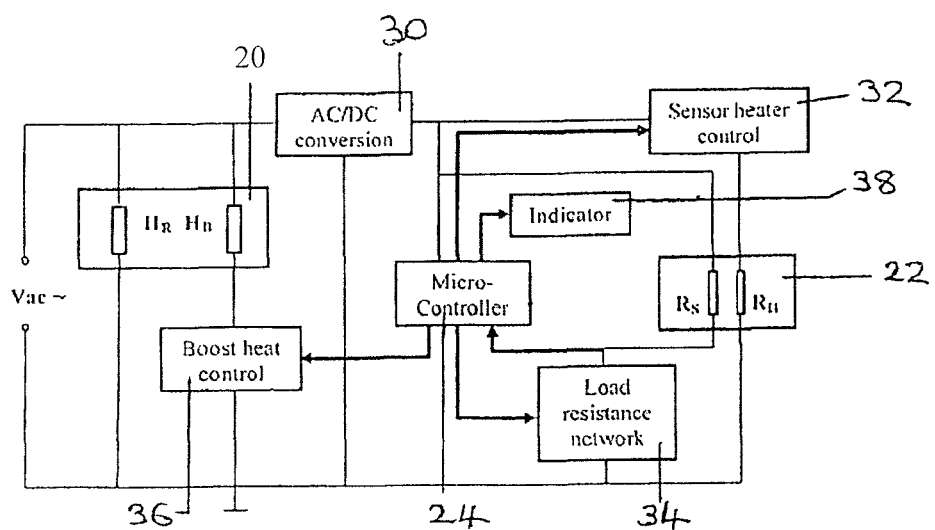
FIG. 2 shows a schematic block diagram of electrical components of the device; and It has been realised that a dispenser for air treatment agents can be made more efficient by using sensing techniques to control when and how much air treatment agents should be dispensed.

FIG. 2 shows a schematic functional layout of the electrical elements of the dispenser. The same reference numerals to those in the physical layout of FIG. 1 have been used where appropriate. The electrical layout is as follows.

The heater 20 provides an elevated temperature for regular emanation (by resistor HR), and a further elevated temperature for boost emanation (by resistors HR and HB); The chemical odour sensor 22, which is a heated element (DC powered) with an on-chip heater (RH), and an odour dependent sensing resistor (RS). The power supply 20 includes an AC-to-DC power conversion unit 30, to provide the required power for the odour sensor 22 and other control elements. The controller 24 is a microcontroller unit (MCU) to acquire the odour dependent signal, and control the functional modules of the device, including: a sensor heater control unit 32, to provide steady power to RH; a load resistance network 34 for selecting appropriate load to RS; a boost heat control unit 36, to determine whether to turn the boost heater (HB) on or off; an indicator 38 to indicate the occurrence of boost events.

When the device is powered, the regular heater (HR) is directly powered by the mains to provide the first elevated temperature for the regular emanation. The AC-to-DC converter 30 turns the AC into the required DC voltage level, to power the sensor 22, the MCU 24 and other control units. When the odour sensor 22 is heated to a pre-defined temperature, an odour dependent signal will be generated through the variation of the sensing resistance of RS, which is regularly picked up by the MCU 24 through the adaptive load resistance network 34, with its actual resistance level matched with the RS values. After the MCU 24 has processed the collected signal sequence (details below), a string of signals are sent to the boost heater control unit 36, to automatically determine whether to turn the boost heater (HB) on or not. In the meantime a control signal is sent to the indicator 38 to signify the operational state of the boost heater The odour signals detected by sensor 22 are processed by MCU 24 using a time based relative variation assessment algorithm. Specifically, the MCU samples a string of timed signals from the sensor at regular intervals, for example, every 1, 3, or 5 sec. This signal string is subsequently grouped into a background string, and a foreground string. The background string contains the latest samples collected over a relatively long period of time, for example, 5, 10, 15, 20, or 30 min. While the foreground contains only the latest few samples, e.g. 5 to 10 of them.

A moving average algorithm is applied to both substrings. Specifically, the MCU averages the two strings over their respective time period each time when a new signal reading is taken. When doing so, the eldest signal reading in each string will be replaced by the latest arrival, so that the averages are always aligned with the latest measurement.

The relative change of the foreground against the background reflects the current status of odour present in the concerned space. This change is calculated by dividing the difference between the average of the fore- and back-ground strings by the average of the latter. A threshold of this relative change is selected to determine whether or not an extra boost release of fragrance over a period of e.g. 5 or 10 min is necessary.

When the current and background readings are available a difference is made between the two and the result is divided by the background value. For ease of comprehension of the value thus obtained, it is multiplied by a constant to provide a more intelligible value. When this weighted difference is greater than a set threshold the boost is triggered.

Similarly, this threshold is the one against which the device initiates itself on first being switched on so for example if a background level of current flowing through the sensor is 600 mA by the average obtained for calculating the threshold, then if the current measurement deviates by more than 100 mA, then the boost may be activated.

As well as the opportunity to set the boost threshold, a fragrance strength adjustability switch may also be provided for the user to achieve a desirable fragrance strength. This fragrance strength adjustability switch may be linked to the duration of the boost provided by the second resistor in the heater block 18 or the frequency of the boost, such the fragrancing level achieved during boost is in proportion to that during normal operation.

An alternative embodiment of air treatment agent dispenser incorporates a container having different air treatment agents. The first air treatment agent may be a fragrance, as referred to above. The second agent may be an odour eliminating composition. The dispenser may be operated by having a permanent release, or steady level of release of the fragrance, with the odour eliminating composition being triggered when the sensor detects an odour event as determined by deviation from the background level as described above.

Advantages of the dispensing devices described above result from the use of a non-specific sensor. Also, the use of twin air treatment agent device assists in giving a pleasant general background fragrance and a means for addressing intermittent odour.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A dispensing device for at least one air treatment agent which device operates to detect the concentration of chemical compounds in the environment surrounding the device, said device comprising:
    at least one airborne agent detector which detects airborne agents in the air in the environment surrounding the device including a current airborne agent level;
    at least one receiving means configured to receive at least one source of an air treatment agent;
    a control means which calculates a background airborne agent level by calculating an average airborne agent level over a longer time period than the current airborne agent level, and which control means releases an amount of the at least one air treatment agent from the source when received in the device and when the control means calculates that a current airborne agent level deviates from a background airborne agent level by more than a predetermined amount.

2. A dispensing device according to claim 1, in which the control means calculates the deviation of the current airborne agent level from the background airborne agent level by subtracting the background level from the current airborne agent level and dividing that amount by the background level value.

3. A dispensing device according to claim 1, in which the control means calculates the current airborne agent level by calculating an average of a predetermined number of most recent readings of the detector.

4. A dispensing device according to according to claim 1, wherein the background airborne agent level is calculated as an average of the levels of airborne agent detected by the device throughout the duration of a particular operational mode of the device.

5. A dispensing device according to claim 1, wherein the control means calculates the background airborne agent level by calculating an average of a predetermined number of some or all of 10 to 10,000 of the most recent readings of the detector.

6. A dispensing device according to claim 1, in which the background airborne agent level and the current airborne agent level are temporally offset.

7. A dispensing device according to claim 1, in which the control means calculates the background airborne agent level based on calculating a series of averages from rolling windows of measurements from the detector.

8. A dispensing device according to claim 7, in which each rolling window is an average of between two and ten readings.

9. A dispensing device according to claim 7, in which the windows do not overlap.

10. A dispensing device according to claim 7, in which the windows span a time period of between 5 and 30 minutes.

11. A dispensing device according to claim 7, in which the control means operates to discard the oldest window when a new window becomes available.

12. A dispensing device according to claim 1, in which the control means operate to adjust the predetermined level of deviation from the background level that results in air treatment agent being released.

13. A dispensing device according to claim 1, in which the control means operate to activate emanation acceleration means.

14. A dispensing device according to claim 1, in which the device further comprises a first heating element which provides a first level of dispensing of at least one air treatment agent.

15. A dispensing device according to claim 14, in which the device further comprises a second heating element, and/or a fan, and wherein at least one of the first heating element, the second heating element and the fan provide a boost to the emanation of at least one air treatment agent, in response to the control means.

16. A dispensing device according to claim 1, wherein the control means cause a background of a first air treatment agent to be dispensed, and a second air treatment agent to be dispersed on detection of the deviation of the current level from the background level.

17. A dispensing device according to claim 1, in which the dispensing device comprises a source of at least one air treatment agent.

18. A dispensing device according to claim 17, in which each source of air treatment agent has its own heater and/or fan to assist dispensing.

19. A dispensing device according to claim 1, wherein the at least one airborne agent detector has a sensor heater.

20. An automated method for dispensing at least one air treatment agent comprising the steps of:
   providing a dispensing device which operates to detect the concentration of chemical compounds in the environment surrounding the device, said device comprising;
   at least one airborne agent detector which detects airborne agents in the air in the environment surrounding the device including a current airborne agent level;
   at least one receiving means configured to receive at least one source of an air treatment agent;
   control means; and,
   operating the device during which the control means calculates a background airborne agent level by calculating an average airborne agent level over a longer time period than the current airborne agent level and, and which control means releases an amount of the at least one air treatment agent from the source when present in the device and when the control means calculates that a current airborne agent level deviates from a background airborne agent level by more than a predetermined amount.

21. A method according to claim 20, in which the airborne agent level is calculated by calculating an average of a predetermined number of the most recent readings of the detector.

22. A method according to claim 20, wherein the background airborne agent level is calculated as an average of the levels of airborne agent detected by the device throughout the duration of a particular operational mode of the device.

23. A method according to claim 20, wherein the control means calculates the background airborne agent level by calculating an average of a predetermined number of some or all of 10 to 10,000 of the most recent readings of the detector.

24. A method according to claim 20, in which the background airborne agent level and the current airborne agent level are temporally offset.

25. A method according to claim 20, in which the background level is calculated based on a series of averages from rolling windows of measurements from the detector.

26. A method according to claim 25, in which the oldest window is discarded when a new window becomes available.

27. A method according to claim 20, wherein the dispensing device comprises a source of at least one air treatment agent.

* * * * *